US00PP25889P3

(12) United States Plant Patent
Mazzardis

(10) Patent No.: US PP25,889 P3
(45) Date of Patent: Sep. 15, 2015

(54) BLUEBERRY PLANT, 'EB 8-30'

(50) Latin Name: ***Vaccinium* Hybrid**
Varietal Denomination: EB 8-30

(71) Applicant: Vincent David Mazzardis, Joondalup (AU)

(72) Inventor: Vincent David Mazzardis, Joondalup (AU)

(73) Assignee: PRUNUS PERSICA PTY LTD, Joondalup (AT)

( * ) Notice: Subject to any disclaimer, the term of this patent is extended or adjusted under 35 U.S.C. 154(b) by 149 days.

(21) Appl. No.: 13/986,852

(22) Filed: Jun. 12, 2013

(65) Prior Publication Data

US 2013/0340128 P1 Dec. 19, 2013

(30) Foreign Application Priority Data

Jun. 14, 2012 (AU) ..... PBR 2012115

(51) Int. Cl.
*A01H 5/00* (2006.01)
*A01H 5/08* (2006.01)

(52) U.S. Cl.
USPC ..... Plt./157
CPC ..... *A01H 5/08* (2013.01)

(58) Field of Classification Search
USPC ..... Plt./157
See application file for complete search history.

(56) References Cited

FOREIGN PATENT DOCUMENTS

AU 2012/115 6/2012

*Primary Examiner* — Annette Para
(74) *Attorney, Agent, or Firm* — Paine Hamblen, LLP

(57) ABSTRACT

A new and distinct variety of blueberry plant, which is denominated varietally hereinafter as 'EB 8-30' is described, and which produces an attractively colored berry, which is mature for harvesting and shipment in the mid-season, and which further is medium to large in size, and wherein the blueberry plant has an semi-upright growth habit, all when grown under the ecological conditions prevailing in Yanchep, Western Australia.

1 Drawing Sheet

Latin name: '*Vaccinium* Hybrid'.
Varietal denomination: 'EB 8-30'.

RELATED APPLICATION DATA

The present application claims priority from Australian Plant Breeders Rights Application Serial No. 2012/115, and which was filed on 14 Jun. 2012.

BACKGROUND OF THE NEW VARIETY

The present invention relates to a new, novel, and distinct variety of blueberry plant '*Vaccinium* Hybrid,' and which has been denominated varietally, hereinafter, as 'EB 8-30'.

ORIGIN AND ASEXUAL REPRODUCTION

The present variety of blueberry plant resulted from an ongoing program of plant development. The purpose of this program is to improve the commercial quality of blueberry plants by creating and releasing promising selections each year, in order to produce plant populations from which improved progenies are evaluated and selected. The new blueberry plant 'EB 8-30' was originated by me and selected from a population of new plants growing on my farm, which is located near Yanchep Springs, Yanchep, Western Australia. The new variety of blueberry plant was derived from a cross that I made in 2005 of the blueberry seed parent 'Compact 36' [unpatented], and the pollen parent, blueberry plant '99-12' [unpatented]. The seed parent is a compact bush which displays early season flowering, and which further produces small to medium sized fruit. On the other hand, the pollen parent is characterized by a semi-spreading growth habit and which further produces large, early maturing fruit. Seed derived from the seed parent 'Compact 36' produced approximately 300 plants. These new plants were grown and the first fruit was evaluated in 2007. Still further, a second assessment was conducted during the 2008 growing season, and this resulted in the selection of 'EB 8-30' as having particularly desirable traits. Subsequently, the new variety 'EB 8-30' was asexually reproduced by cuttings and these further plants were assessed during subsequent 2009 through 2012 growing seasons. These further evaluations led to the conclusion that the new variety 'EB 8-30' is a distinct and suitable commercial variety for commercial, and retail use.

In relative comparison to the seed parent, 'Compact 36', the new variety 'EB 8-30' is principally characterized as a novelty by producing fruit which are mature for harvesting in the mid-season, and further produces medium to large fruit, and which additionally displays a compact growth habit. In contrast, the seed parent produces fruit which are ripe for harvesting in the mid to late season, and has a fruit size which is only average to medium, and further has a semi-upright growth habit. In relative comparison to the pollen parent blueberry plant '99-12,' the new variety 'EB 8-30' again produces fruit in the mid-season, which is medium to large in size, and which further has a compact growth habit. However, the pollen parent produces fruit which are ripe for harvesting in the mid to late season; produces small to medium sized fruit; and has a growth habit which is considered more upright.

BRIEF DESCRIPTION OF THE DRAWING

FIG. 1 depicts six whole fruit sufficiently matured for harvesting and shipment, a twig bearing typical leaves showing the dorsal and ventral coloration, and growth habit thereof, and five leaves showing the dorsal and ventral coloration thereof. In addition, FIG. 1 shows the closest known variety, that being to 'Sharpeblue' blueberry plant [unpatented], which again shows six fruit which are sufficiently mature for harvesting and shipment, a twig bearing typical leaves, and five leaves showing the dorsal and ventral coloration so that the two blueberry varieties can be compared, one with the other.

The color in this photograph is as nearly true as is reasonably possible in a color representation of this type. Due to chemical development, processing and printing, the leaves and fruit depicted in these photographs, may or may not be accurate when compared to the actual specimen. For this reason, future color references should be made to the color descriptions as provided in The Royal Horticulture Society Colour Charts ($5^{th}$ Edition) hereinafter.

NOT A COMMERCIAL WARRANTY

The following detailed description has been prepared to solely comply with the provisions of 35 U.S.C. §112 and does not constitute a commercial warranty (either expressed or implied), that the present variety will, in the future, display the botanical, horticultural or other characteristics as set forth, hereinafter. Therefore, this disclosure may not be relied upon to support any future legal claims including, but not limited to, breach of warranty of merchantability, or fitness for any particular purpose, or non-infringement, which is directed, in whole, or in part, to the present new variety.

DETAILED DESCRIPTION

Referring more specifically to the botanical details of this new and distinct variety of blueberry plant, the following has been observed during the sixth fruiting season, under the ecological conditions prevailing at my farm, which is located near Yanchep Springs, Western Australia. Common color names are also occasionally used.

PLANT

Plant vigor: Considered average for the species. This is in contrast to the closest known variety the 'Sharpeblue' blueberry plant, and which has a displayed plant vigor which is considered medium to strong.

Plant growth habit: Considered semi-upright. This is in contrast to the closest known variety which has an upright growth habit.

*Average plant size*.—1.6 meters in height, and 1.2 meters in width.

One year old shoots:

*Color*.—Yellow-Green, (RHS 145A).

One year old shoots:

*Internode length*.—Considered average for the species. This is in contrast to the closest known variety, as noted above, and which has internode lengths that are considered medium to long.

LEAF

Leaf length: Considered average for the species, about 56 mm. This is in contrast to the closest known variety, which displays a leaf length which is considered to be medium to long.

Leaf width: Considered narrow to medium for the species, about 30 mm. This is in contrast to the closest known variety the 'Sharpeblue' blueberry plant, which has a leaf width which is considered medium to broad. This distinction can be best seen in FIG. 1.

Leaf shape:

*Generally*.—Considered ovate.

Leaf color:

*Dorsal surface*.—Green.

Leaf color:

*Dorsal surface*.—Considered medium to dark green (RHS N134A). This is in contrast to the closest known variety which has a color intensity which is considered light to medium green. This can be seen most clearly by reference to FIG. 1.

*Leaf color*.—Ventral Surface — Green (RHS 138B).

Leaf marginal edge:

*Generally speaking*.—Entire.

FLOWERS

Flower bud anthocyanin coloration: Considered very weak.

*Open flower color*.—White (RHS NN155C).

Inflorescence:

*Length*.—Considered short to medium for the species, about 13 mm. This is in contrast to the closest known variety that typically produces an inflorescence, which is considered average for the species.

*Average flower width*.—About 8 mm.

Corolla shape: Urceolate.

*Corolla length*.—About 11 mm.

Corolla size: Considered medium for the species. This is in contrast to the closest known variety where the corolla size is considered medium to large.

Anthocyanin coloration of the corolla tube: Generally speaking, it is considered very weak to weak.

Ridges on the corolla tube: Present.

Fruit clusters:

*Density*.—Considered average for the species. This is in contrast to the fruit cluster densities as displayed by the 'Sharpeblue' blueberry plant, which is considered to be dense.

Color intensity:

*Unripe fruit*.—Considered average for the species, green (RHS 142B). In contrast, the closest known variety displays a similar characteristic, which is considered only light to medium green.

Fruit size:

*Generally*.—Considered medium to large, about 18 mm. This is in contrast to the 'Sharpeblue' blueberry plant, which produces fruit having a size which is only considered average for the species.

Fruit shape:

*Longitudinal sectional view*.—Considered oblate.

Fruit:

*Sepal orientation*.—Considered erect.

Sepal type:

*Considered straight.*

Calyx diameter: Considered small to medium for the about, 6 mm.

Calyx basin depth: Considered shallow, about 2 mm. This is in contrast to the closest known variety which has a calyx basin depth which is considered average for the species.

Intensity of bloom: Considered strong.

Fruit skin coloration: Considered dark blue-black (RHS 203D).

Fruit firmness: Considered firm for the species. This is in contrast to the closest known variety which produces fruit having a firmness, which is considered soft to medium.

Fruit sweetness: Considered high for the species. This is in contrast to the closest known variety where the fruit sweetness is considered merely average.

*Color of fruit flesh.*—Yellow-Green (RHS 145B).

Fruit acidity: Considered low for the species. This is in contrast to the closest known variety where the same displayed characteristic is considered to be average.

*Color of seeds.*—Brown (RHS 200C).

Fruiting type: On one year old and current season shoots.

Vegetative bud burst: Considered very early for the species. This is in contrast to the closest known variety where this displayed characteristic is merely only early for the species.

Beginning of flowering on one year old and older shoots: Considered very early in the season. This is in contrast to the closest known variety where the time of flowering is merely just early.

Beginning of flowering time on current year's shoots: Considered very early. This is in contrast to the closest known variety where the same characteristic is merely only early.

Beginning of fruit ripening on one year old shoots: Considered very early in the season. This is in contrast to the closest known variety where this same characteristic is early to the mid-season dates of the growing season.

Beginning of fruit ripening on current year's shoots: Considered very early. This is a date earlier in time than the same date for the closest known variety.

Resistance to insects and disease: No particular susceptibilities were noted. The present variety has not been tested to expose or detect any susceptibilities or resistances to any known plant and/or fruit diseases.

Although the new variety of blueberry plant possesses the described characteristics when grown under the ecological conditions prevailing near Yanchep Springs, Western Australia, it should be understood that variations of the usual magnitude and characteristics incident to changes in growing conditions, fertilization, pruning, pest control, frost, climatic variables and horticultural management are to be expected.

Having thus described and illustrated my new variety of blueberry plant, what I claim is new and desire to secure by Plant Letters Patent is:

1. A new and distinct variety of blueberry plant, substantially as illustrated and described and which is characterized principally as to novelty by producing a blueberry plant which is mature for harvesting in the mid-season, and which further produces medium to large fruit, and has an upright growing habit, all when grown under the ecological conditions prevailing in Yanchep, Western Australia.

* * * * *

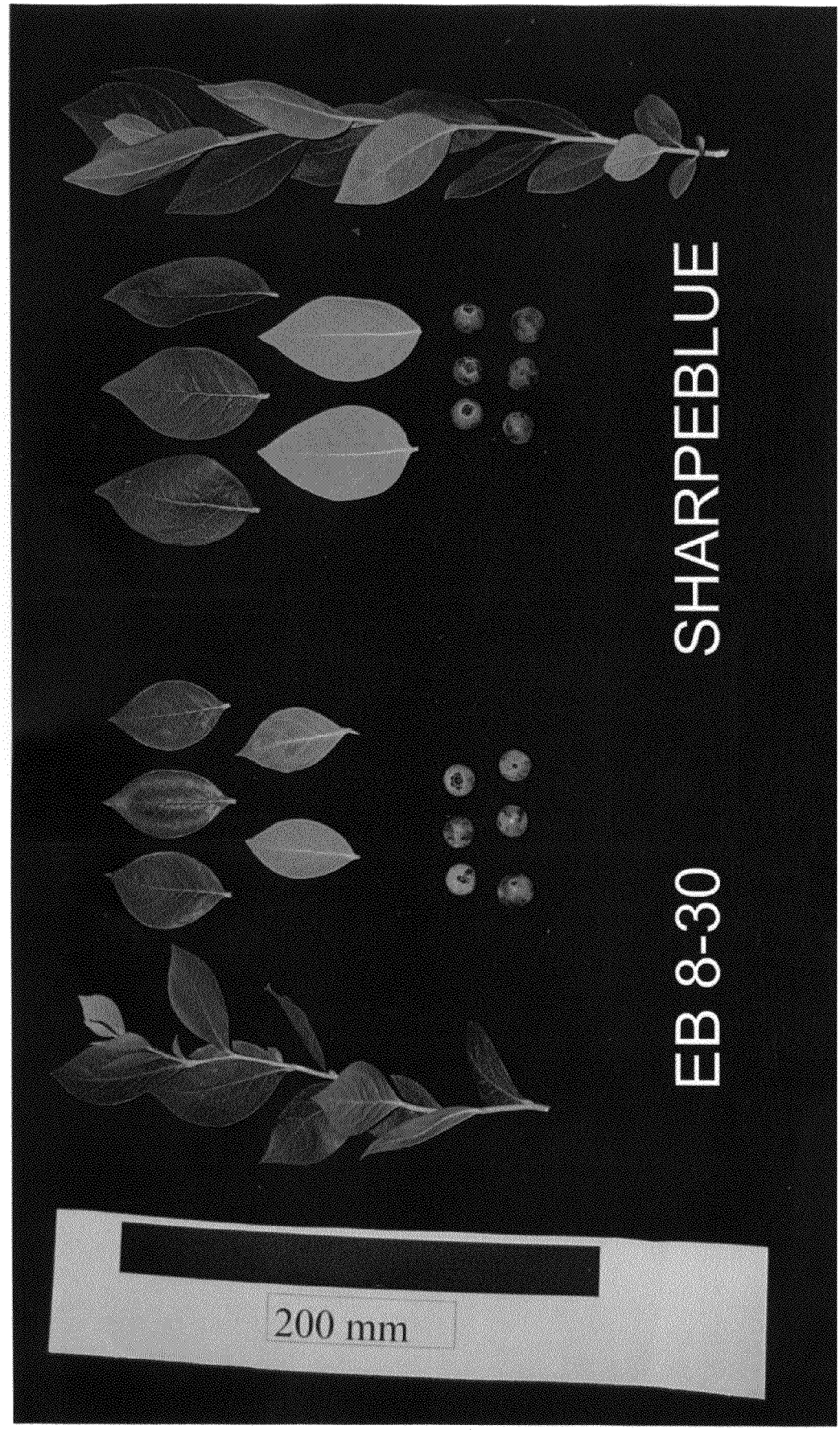
EB 8-30
SHARPEBLUE
200 mm